United States Patent
Biedermann et al.

(10) Patent No.: US 9,155,568 B2
(45) Date of Patent: Oct. 13, 2015

(54) BONE ANCHORING DEVICE

(75) Inventors: Lutz Biedermann, VS-Villingen (DE); Helmar Rapp, Deiβlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/073,503

(22) Filed: Mar. 28, 2011

(65) Prior Publication Data

US 2011/0251650 A1    Oct. 13, 2011

Related U.S. Application Data

(60) Provisional application No. 61/318,621, filed on Mar. 29, 2010.

(30) Foreign Application Priority Data

Mar. 29, 2010 (EP) ..................... 10158250

(51) Int. Cl.
*A61B 17/70* (2006.01)

(52) U.S. Cl.
CPC .................................. *A61B 17/7037* (2013.01)

(58) Field of Classification Search
CPC ............... A61B 17/70; A61B 17/7001; A61B 17/7032; A61B 17/7034; A61B 17/7035; A61B 17/7037; A61B 17/7038; A61B 17/7041; A61B 17/7043; A61B 17/7046
USPC ........... 606/246, 247, 250–279, 300–320, 99, 606/104, 86 A, 90
See application file for complete search history.

(56) References Cited

U.S. PATENT DOCUMENTS 5,129,388 A    7/1992   Vignaud et al.
5,480,401 A    1/1996   Navas
(Continued)

FOREIGN PATENT DOCUMENTS

CA    2133484    1/1995
CN    1098894 A   2/1995
(Continued)

OTHER PUBLICATIONS

Extended European Search Report and Opinion mailed Jun. 14, 2010 for EPO Application No. EP 10 158 250.0, 6 sheets.
(Continued)

*Primary Examiner* — Pedro Philogene
*Assistant Examiner* — Lynnsy Summitt
(74) *Attorney, Agent, or Firm* — Christie, Parker & Hale, LLP (57) ABSTRACT

A bone anchoring device includes an anchoring element having a shaft and a head; a receiving part having a top end, a bottom end, a rod recess, a coaxial bore, and a seat; and a pressure element that is movable within the bore. The head is pivotable with respect to the receiving part and can be fixed at an angle by exerting pressure via the pressure element onto the head. The pressure element has an outer wall portion having a recess or a projection. The receiving part has an inner wall portion having a recess or a projection that cooperates with the recess or projection of the pressure element. The pressure element is configured to assume a first position within the receiving part in which the recess and the projection interact to allow the pressure element to exert a preload onto the head and the head is prevented from freely pivoting but is not locked.

20 Claims, 5 Drawing Sheets

(56) References Cited

U.S. PATENT DOCUMENTS

| | | | | |
|---|---|---|---|---|
| 5,647,873 A * | 7/1997 | Errico et al. | | 606/264 |
| 5,672,176 A * | 9/1997 | Biedermann et al. | | 606/271 |
| 5,690,630 A * | 11/1997 | Errico et al. | | 606/264 |
| 5,716,356 A | 2/1998 | Biedermann et al. | | |
| 5,817,094 A * | 10/1998 | Errico et al. | | 606/264 |
| 5,873,878 A * | 2/1999 | Harms et al. | | 606/308 |
| 5,879,350 A * | 3/1999 | Sherman et al. | | 606/270 |
| 5,961,517 A | 10/1999 | Biedermann et al. | | |
| 6,132,432 A * | 10/2000 | Richelsoph | | 606/278 |
| 6,440,137 B1 * | 8/2002 | Horvath et al. | | 606/302 |
| 6,837,889 B2 * | 1/2005 | Shluzas | | 606/270 |
| 7,087,057 B2 * | 8/2006 | Konieczynski et al. | | 606/278 |
| 7,604,656 B2 | 10/2009 | Shluzas | | |
| 7,691,129 B2 * | 4/2010 | Felix | | 606/246 |
| 7,875,065 B2 * | 1/2011 | Jackson | | 606/305 |
| 7,942,911 B2 * | 5/2011 | Doubler et al. | | 606/269 |
| 7,955,363 B2 * | 6/2011 | Richelsoph | | 606/305 |
| 7,967,850 B2 * | 6/2011 | Jackson | | 606/301 |
| 8,016,862 B2 * | 9/2011 | Felix et al. | | 606/270 |
| 8,066,744 B2 * | 11/2011 | Justis et al. | | 606/266 |
| 8,075,599 B2 * | 12/2011 | Johnson et al. | | 606/266 |
| 8,080,040 B2 * | 12/2011 | Miller | | 606/272 |
| 8,100,948 B2 * | 1/2012 | Ensign et al. | | 606/267 |
| 8,137,387 B2 * | 3/2012 | Garamszegi | | 606/270 |
| 8,167,916 B2 * | 5/2012 | Saint-Martin | | 606/279 |
| 8,197,517 B1 * | 6/2012 | Lab et al. | | 606/268 |
| 8,236,035 B1 * | 8/2012 | Bedor | | 606/328 |
| 8,257,396 B2 * | 9/2012 | Jackson | | 606/246 |
| 2004/0249380 A1 * | 12/2004 | Glascott | | 606/73 |
| 2004/0267264 A1 | 12/2004 | Konieczynski et al. | | |
| 2006/0293665 A1 * | 12/2006 | Shluzas | | 606/61 |
| 2007/0173819 A1 * | 7/2007 | Sandlin | | 606/61 |
| 2007/0225711 A1 * | 9/2007 | Ensign | | 606/61 |
| 2007/0270813 A1 * | 11/2007 | Garamszegi | | 606/61 |
| 2008/0045953 A1 * | 2/2008 | Garamszegi | | 606/61 |
| 2008/0243193 A1 * | 10/2008 | Ensign et al. | | 606/305 |
| 2008/0269809 A1 * | 10/2008 | Garamszegi | | 606/305 |
| 2009/0062867 A1 * | 3/2009 | Schumacher | | 606/308 |
| 2009/0069853 A1 * | 3/2009 | Schumacher | | 606/301 |
| 2009/0105716 A1 * | 4/2009 | Barrus | | 606/103 |
| 2009/0318969 A1 | 12/2009 | Matthis et al. | | |
| 2010/0036433 A1 | 2/2010 | Jackson | | |
| 2010/0094349 A1 * | 4/2010 | Hammer et al. | | 606/264 |
| 2010/0131018 A1 * | 5/2010 | Konieczynski et al. | | 606/308 |
| 2010/0179602 A1 * | 7/2010 | Dauster et al. | | 606/308 |
| 2010/0191290 A1 * | 7/2010 | Felix | | 606/264 |
| 2010/0228293 A1 * | 9/2010 | Courtney et al. | | 606/264 |
| 2011/0106176 A1 * | 5/2011 | Jackson | | 606/305 |
| 2011/0218578 A1 * | 9/2011 | Jackson | | 606/305 |
| 2011/0218579 A1 * | 9/2011 | Jackson | | 606/305 |
| 2011/0282399 A1 * | 11/2011 | Jackson | | 606/305 |
| 2012/0035670 A1 * | 2/2012 | Jackson et al. | | 606/305 |
| 2012/0041490 A1 * | 2/2012 | Jacob et al. | | 606/264 |
| 2012/0046700 A1 * | 2/2012 | Jackson et al. | | 606/305 |
| 2012/0059426 A1 * | 3/2012 | Jackson et al. | | 606/300 |
| 2012/0143266 A1 * | 6/2012 | Jackson et al. | | 606/328 |
| 2012/0209336 A1 * | 8/2012 | Jackson et al. | | 606/305 |

FOREIGN PATENT DOCUMENTS

| | | |
|---|---|---|
| CN | 101606860 A | 12/2009 |
| EP | 0 611 554 A1 | 8/1994 |
| JP | 2007-526007 A | 9/2007 |
| WO | WO 90/09156 A1 | 8/1990 |
| WO | WO 2005/004699 A2 | 1/2005 |
| WO | WO 2006/116437 A2 | 11/2006 |
| WO | WO 2008/008511 A2 | 1/2008 |
| WO | WO 2009/015100 A2 | 1/2009 |

OTHER PUBLICATIONS

Extended European Search Report and Opinion mailed May 24, 2013 for EPO Application No. EP 13 158 853.5, 6 sheets.

* cited by examiner

BONE ANCHORING DEVICE

CROSS-REFERENCE TO RELATED APPLICATIONS

This Application claims priority to and the benefit of U.S. Provisional Application No. 61/318,621, filed Mar. 29, 2010, the entire contents of which are incorporated herein by reference. This Application also claims priority to and the benefit of EP 10 158 250.0, filed in the European Patent Office on Mar. 29, 2010, the entire contents of which are incorporated herein by reference.

BACKGROUND

The invention relates to a bone anchoring device for anchoring a stabilization rod in a bone or in a vertebra. The bone anchoring device includes an anchoring element and a receiving part for receiving a head of the bone anchoring element and for receiving a stabilization rod to be connected to the anchoring element. The anchoring element is pivotably connected to the receiving part and can be fixed at an angle by exerting pressure onto the head via a pressure element that is arranged in the receiving part. The pressure element and the receiving part have recesses and projections that are configured to cooperate in such a way that the pressure element can assume a position within the receiving part in which it clamps the head by friction without locking it.

U.S. Pat. No. 5,716,356 describes a polyaxial bone screw including a screw element, a receiving part that is pivotably connected to the screw element, and a pressure element to exert pressure onto the head of the screw element to fix the angle between the screw element and the receiving part. The receiving part has a U-shaped channel for receiving a stabilization rod. The pressure element comprises a cylindrical recess that is to be aligned with the U-shaped channel to receive the rod therein. In order to hold the pressure element in a position aligned with the U-shaped channel, the position of the pressure element is fixed by crimping through bores provided in the receiving part.

U.S. Pat. No. 5,672,176 describes another example of a polyaxial bone screw with a pressure element that is also held in place by crimp bores without impeding a sufficient movement of the pressure element to clamp the head. The receiving part has a tapering inner surface portion and the pressure element has a correspondingly tapering outer surface in a region laterally surrounding said screw head. By the cooperating tapering surfaces, the head can be locked while still allowing adjustments of the position of the rod.

WO 2006/116437 A2 describes a bone anchor for spinal fixation in the form of a polyaxial bone screw including screw element, a housing, a sleeve and a collet arranged in the housing for exerting pressure onto the head of the screw element. The sleeve has retention tabs that snap into slots in opposite wall portions of the housing.

If the head of the anchoring element is freely pivotable with respect to the receiving part, the alignment of the receiving part and the insertion of the rod may be difficult in more complex clinical applications, for example, when a multitude of bone anchors have to be connected to the rod.

U.S. Pat. No. 7,604,656 describes a fastener engageable with a bone portion to connect a longitudinal member to the bone portion. The housing that receives the fastener also receives a spacer that is engageable with the fastener and the longitudinal member. In one embodiment the spacer is urged by a pin member into frictional engagement with the fastener and with the housing.

SUMMARY

It is an object of the invention to provide a bone anchoring device that allows for an improved handling during surgery and that can be manufactured in a simple manner.

With the bone anchoring device, a temporary clamping of the head in an appropriate angular position with respect to the receiving part without locking the head can be achieved. This allows the receiving part to be held in an adjustable angular position. In this position the pressure element exerts a preload onto the head, in which the head is not locked but prevented from freely pivoting. When the head is temporarily clamped, the alignment of the receiving parts to the rod and the insertion of the rod are facilitated. Also, when the rod is already inserted into the receiving part, adjustments of the rod are still possible without completely loosening the head within the receiving part. Finally, the pressure element can be pressed onto the head to lock the head in its desired position.

In addition, the bone anchoring device has only few parts, which are of simple design. The bone anchoring device must not necessarily be preassembled but can be assembled in any condition of the delivery after the parts have been manufactured and before the screw element is inserted into the bone. The pressure element can even be disassembled from the receiving part without having to apply large forces. Therefore, the assembling of the polyaxial bone screw can be carried out by any specialist, for example by the surgeon or any personnel assisting him or her before or during surgery.

With the bone anchoring device, a modular system can be provided that allows the combination of various anchoring elements with any suitable receiving part, depending on the actual clinical requirements. This reduces the costs of polyaxial screws, reduces the inventory and gives the surgeon a substantial choice of implants.

The receiving part and the pressure element can be manufactured in series at low costs.

Further features and advantages of the invention will become apparent from the description of embodiments by means of the accompanying drawings.

DETAILED DESCRIPTION

Figure 1:
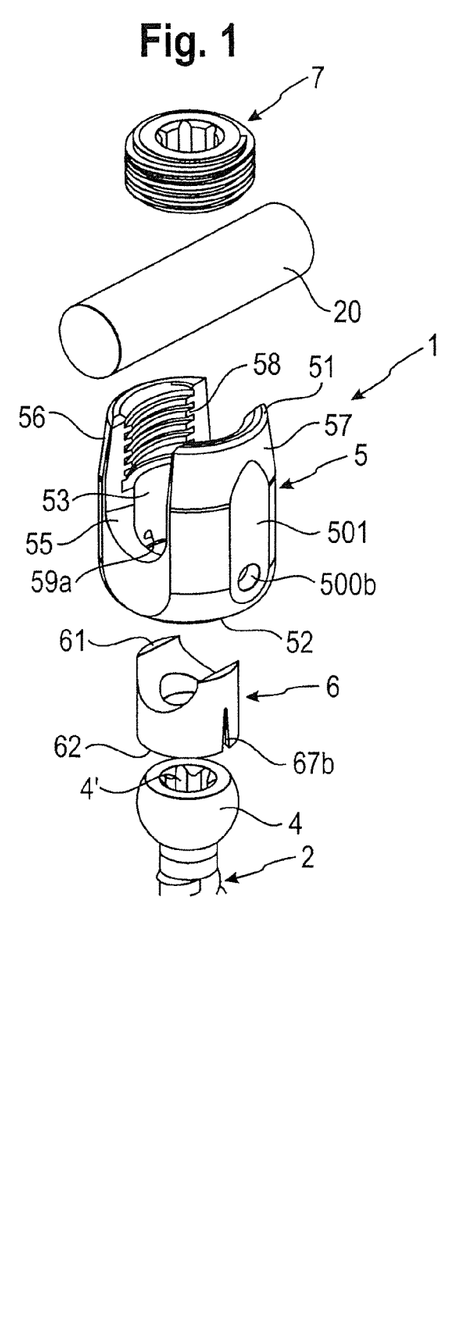
FIG. 1 shows a perspective exploded view of an embodiment of the bone anchoring device.
Figure 2:
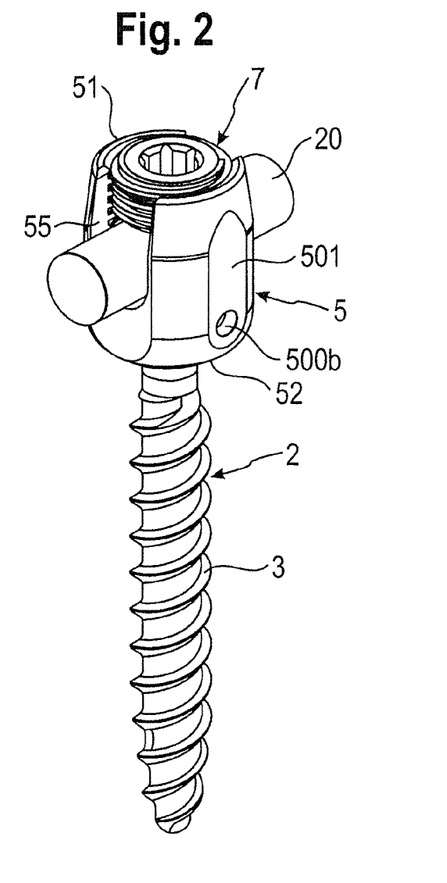
FIG. 2 shows the bone anchoring device of FIG. 1 in an assembled state.
Figure 3:
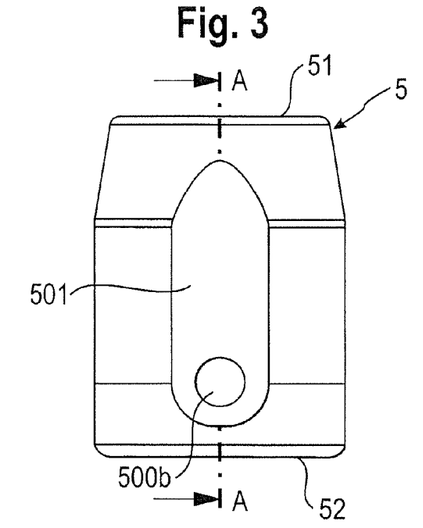
FIG. 3 shows a side view of the receiving part of the bone anchoring device of FIG. 1.
Figure 4:
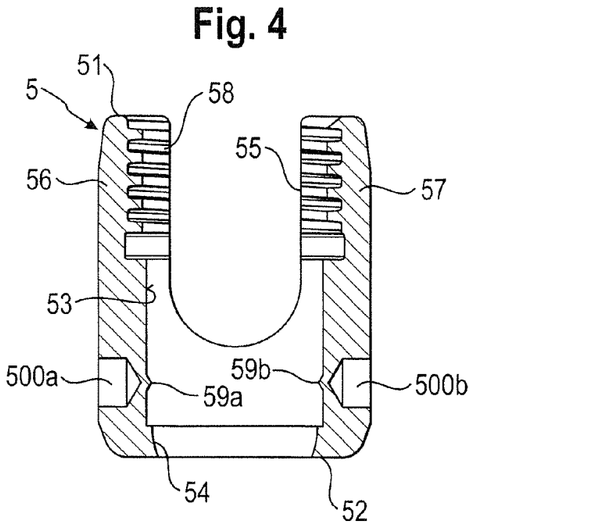
FIG. 4 is a sectional view of the receiving part along line A-A in FIG. 3.
Figure 5:
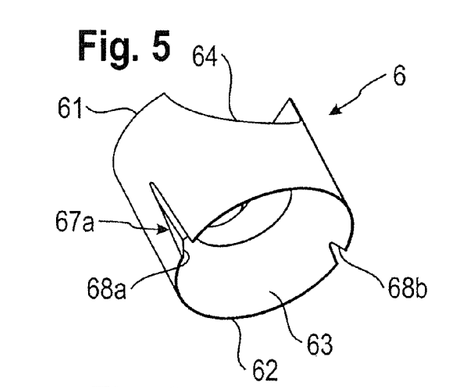
FIG. 5 is a perspective view of the pressure element of the bone anchoring device.

The bone anchoring device 1 according to an embodiment shown in FIGS. 1 and 2 includes a bone anchoring element in the form of a screw member 2 having a threaded shaft 3 and a head 4. The head 4 is, for example, shaped as a spherical segment. The head 4 has a recess 4' at its free end for engagement with a tool (not shown). The bone anchoring device 1 further includes a receiving part 5 for connecting the screw member 2 to a rod 20. A pressure element 6 is arranged in the receiving part 5 on top of the head 4. For securing the rod 20 in the receiving part 5 and for exerting pressure onto the head 4, a locking device in the form of an inner screw 7 that cooperates with receiving part 5 is provided.

The receiving part 5 as shown in particular in FIGS. 1 to 4 is substantially cylindrical and has a top end 51, a bottom end 52 and a coaxial bore 53 that is followed by a seat portion 54 for accommodating the head 4 of the screw member 2. At the seat portion 54 the bore narrows towards the bottom end 52. The seat portion 54 can be a spherically-shaped or tapered or can have any other shape that allows the accommodation of the head 4 so that the head 4 can pivot with respect to the receiving part 5. The receiving part 5 further has at the top end 51 a substantially U-shaped recess 55 by means of which two free legs 56, 57 form the side walls of a channel for receiving the rod 20. An internal thread 58 is provided at the legs 56, 57 for cooperating with the inner screw 7 of the locking device.

The receiving part 5 further comprises at the inner wall of the bore 53, at a distance from the bottom end 52 that is smaller than the distance from the top end 51, two projections 59a, 59b, which are substantially tip-shaped and which project into the interior of the receiving part 5. The projections 59a, 59b are arranged at 180° offset from each other and at 90° with respect to the channel formed by the U-shaped recess 55. The projections 59a, 59b are manufactured, for example, by crimping using crimp bores 500a, 500b at the outside of the receiving part 5 in a manner described below. The receiving part 5 may have flat surface portions 501 at the outer side that extend into the legs 56, 57. The flat surface portions 501 may serve for engagement with a tool (not shown).

The pressure element 6 is formed in one piece. It is of substantially cylindrical construction and has an outer diameter that allows it to move in the axial direction within the bore 53 of the receiving part 5. The pressure element 6 has a top end 61 and a bottom end 62. At the bottom end 62, which faces the head 4 of the screw element 2, a spherical recess 63 is provided that is adapted to the size of the head 4. At the top end 61, a cylindrical recess 64 configured to receive the rod 20 therein is provided. Further, the pressure element 6 has a coaxial bore 65 for allowing access to the screw head 4 with a tool (not shown).

Figure 6:
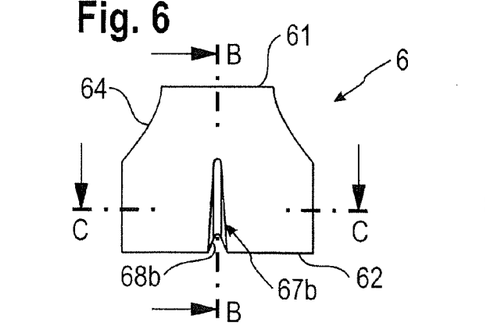
FIG. 6 shows a side view of the pressure element of FIG. 5.
Figure 7:
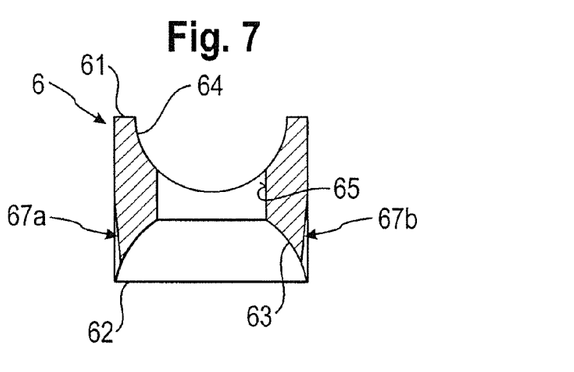
FIG. 7 shows a sectional view of the pressure element, the section being taken along line B-B in FIG. 6.
Figure 8:
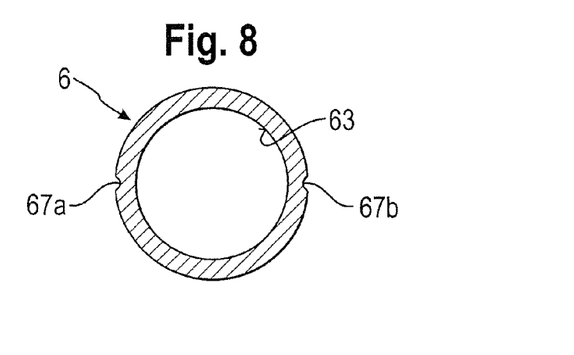
FIG. 8 shows a sectional view of the pressure element, the section being taken along line C-C in FIG. 6.

The pressure element 6 has two coaxially extending recesses in the form of notches 67a, 67b in its outer surface on both sides of the cylindrical recess 64. The notches are open towards the bottom end 62 and are closed at a distance from the bottom end 62. The notches 67a, 67b have a substantially V-shaped cross section and are inclined in such a way that the depth decreases in the direction towards the top end 61 as can be seen in particular in FIGS. 6, 7, 10 and 11. In a portion adjacent the bottom end 62, the notches 67a, 67b extend completely through the pressure element so as to form slits 68a, 68b that facilitate the engagement with the projections 59a, 59b of the receiving part. In a side view as can be seen in FIG. 6, the contour of the notches 67a, 67b at the outer surface of the pressure element 6 is triangular with a small acute angle towards the top end 61. The overall length of the notches 67a, 67b is, for example, approximately half of the height of the pressure element 6.

Figure 10:
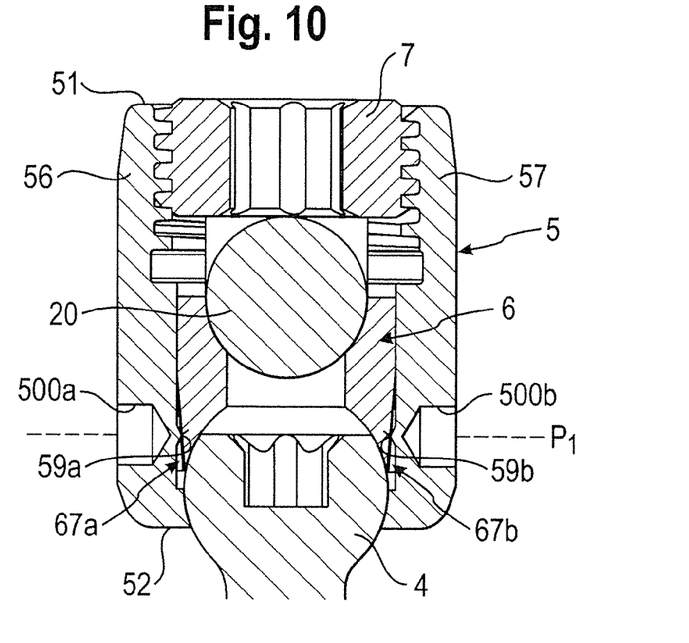
FIG. 10 shows a sectional view of the bone anchoring device of FIG. 1 in an assembled state with the bone anchor
Figure 11:
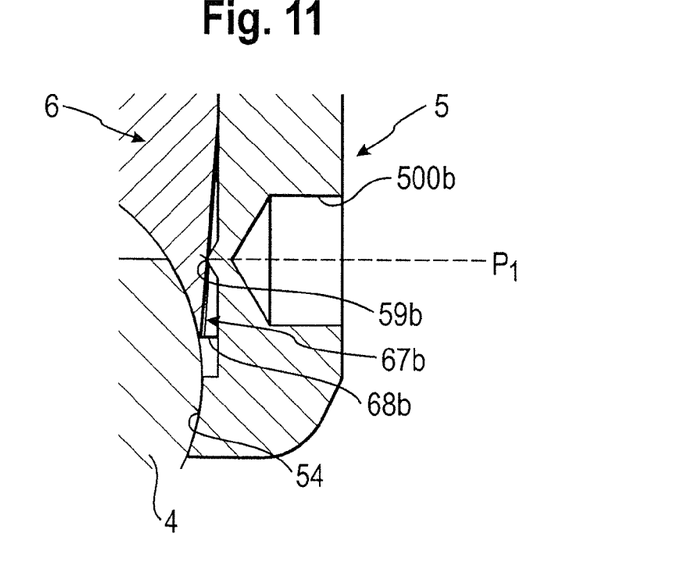
- FIG. 11 shows an enlarged view of a portion of FIG. 10.

The size of the projections 59a, 59b and their position in the receiving part 5 and the size of the notches 67a, 67b is such that the projections 59a, 59b accurately fit into the notches 67a, 67b when the pressure element 6 is inserted into the receiving part 5 and the projections engage the slits 68a, 68b and the lower portions of the notches 67a, 67b. The height of the projections 59a, 59b measured from the surface of the inner wall of the bore 53 is designed such that at a predefined first position P1, as shown in FIGS. 10 and 11, when the pressure element 6 is inserted into the receiving part 5, the projections 59a, 59b have a slight oversize with respect to the depth of the notches 67a, 67b. The position P1 is defined in such a way that the engagement between the projections 59a, 59b and the notches 67a, 67b provides an interference fit that holds the pressure element 6 in the position P1 such that it exerts a preload onto the head 4. By means of the preload exerted by the pressure element 6 onto the head 4, the head is prevented from freely pivoting within the receiving part but is not yet locked. In the position P1, the receiving part can be pivoted with respect to the head 4 by exerting an additional force by hand onto the receiving part.

The projections 59a, 59b in the receiving part 5 are located, as can be seen in particular in FIG. 10, in the region of the upper portion of the head 4 when the screw member 2 is inserted into the receiving part 5. Furthermore, the notches 67a, 67b are formed in the outer wall of the pressure element 6 in the region that has the spherical recess 63. This ensures that at the position P1 the pressure element 6 can exert sufficient pressure for temporary clamping of the head 4. By selecting the position of the projections 59a, 59b, the size of the notches 67a, 67b, and the overall size of the pressure element 6 with respect to each other before the manufacture, the amount of preload exerted onto the head 4 can be defined.

The receiving part 5 and the pressure element 6 are solid parts so that the cooperation between the projections 59a, 59b and the notches 67a, 67b is achieved without spring portions provided at the receiving part 5 or the pressure element 6. Both the receiving part 5 and the pressure element 6 are one-part elements having the projections 59a, 59b and the notches 67a, 67b, respectively, formed integrally therein.

The arrangement of the projections 59a, 59b and of the notches 67a, 67b with respect to the channel axis of the U-shaped recess 55 of the receiving part 5 allows for correct alignment of the recess 64 of the pressure element 6 with respect to the U-shaped recess 55 of the receiving part 5 when inserting the pressure element 6 from the first end 61 into the receiving part 5. Further, the pressure element 6 is secured against rotation within the receiving part 5.

Figure 9A:
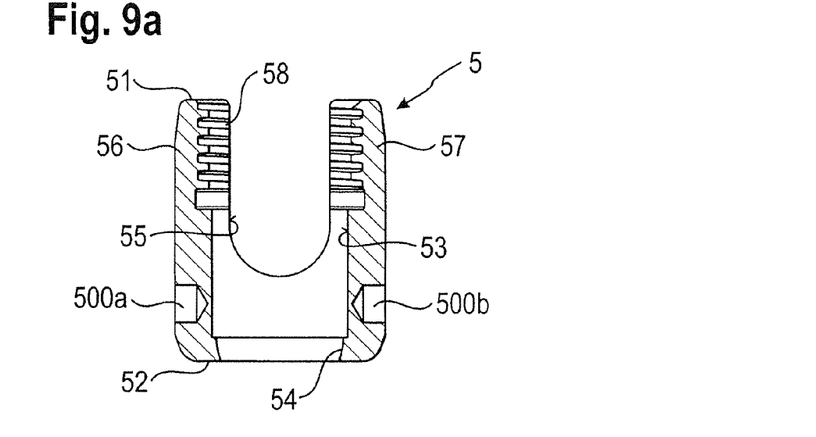
FIGS. 9a) to 9c) show steps of manufacturing the projections in the receiving part of the bone anchoring device in a schematic sectional view.
Figure 9B:
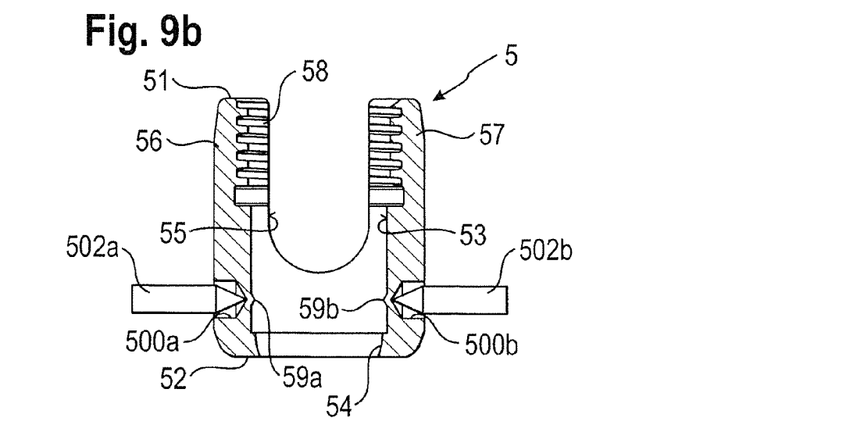
Figure 9C:
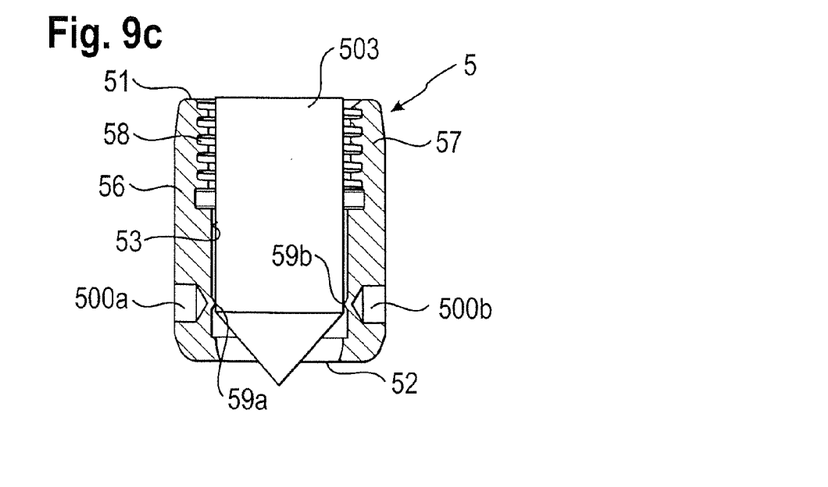

The manufacturing of the projections 59a, 59b to achieve the predefined height is now described with reference to FIGS. 9a) to 9c). The receiving part 5 is first manufactured, for example in a conventional manner by cutting.

Then, the crimp bores 500a, 500b are provided. As shown in FIG. 9b), crimping via crimping tools 502a, 502b is carried out to produce the projections 59a, 59b projecting into the interior of the receiving part 5. Thereafter, a calibration tool 503 is introduced into the receiving part 5 from the first end 51 as shown in FIG. 9c). The calibration tool 503 has an outer diameter that is selected such that the projections 59a, 59b that are formed initially by crimping are deformed so as to obtain the predefined height to be slightly oversized with respect to the depth of the notches 67a, 67b at the position P1.

Figure 12A:
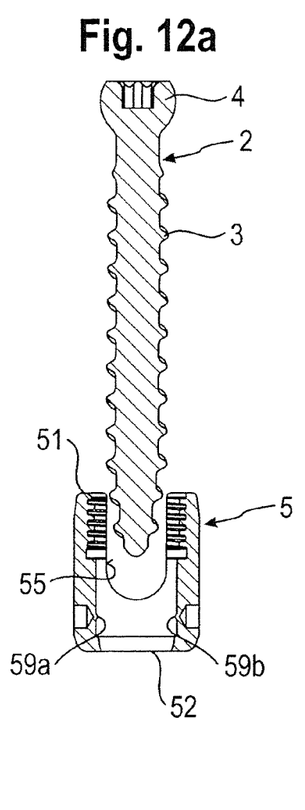
FIGS. 12a) to 12d) show steps of assembling the bone anchoring device.
Figure 12B:
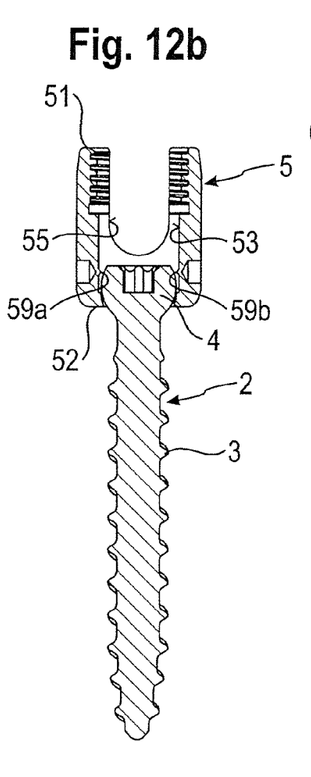

The assembly of the bone anchoring device 1 will now be explained with reference to FIGS. 12a) to 12d). First, as shown in FIG. 12a) the screw member 2 is introduced from the top end 51 into the bore 53 of the receiving part 5 until it rests in the seat 54 as shown in FIG. 12b).

Figure 12C:
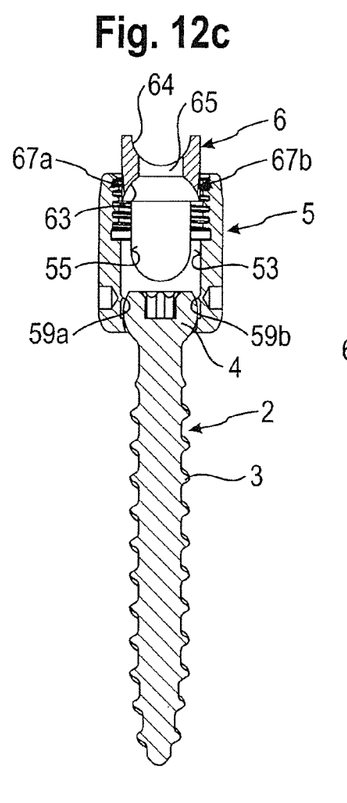
Figure 12D:
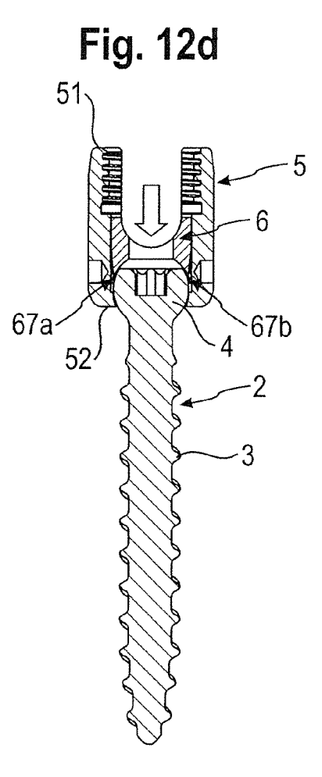

Then, as shown in FIG. 12c) the pressure element 6 is inserted from the top end 51 into the bore 53 of the receiving part 5. A tool (not shown) may be used for insertion and shifting down the pressure element 6. The orientation of the pressure element 6 within the receiving part 5 is such that the notches 67a, 67b and the projections 59a, 59b are aligned. When the pressure element 6 is shifted downwards, as shown in particular in FIG. 12d), the projections 59a, 59b engage the notches 67a, 67b so that the pressure element 6 is guided in the aligned orientation downwards. When the position P1 is reached, due to the slight oversize of the projections 59a, 59b with respect to the notches 67a, 67b, an interference fit between the projections 59a, 59b and the notches 67a, 67b is achieved. In this position P1 the pressure element 6 presses slightly onto the head 4 so that the head 4 can no longer freely pivot as possible before reaching the position P1. The head 4 is held by friction in the position P1. In the position P1, removal of the pressure element 6 is possible by exerting pressure on it from the bottom, for example, with the screw head 4, to loosen the interference fit between projections 59a, 59b and the notches 67a, 67b.

The design of the bone anchoring device 1 allows for assembly and disassembly of the parts of the bone anchoring device in an easy manner. Therefore, the bone anchoring device 1 can be selectively assembled from different receiving parts and screw members at any time after the desired parts have been selected prior to the surgical insertion.

All parts of the bone anchoring device 1 are made of a body-compatible material, such as a body-compatible metal, for example, titanium; body-compatible metal alloys such as, for example, Nitinol; or from a body-compatible plastic material, such as, for example, PEEK; or combinations thereof.

In use, first, the bone anchoring device 1 is provided with the pressure element 6 being in the position P1 in which the head 4 is temporarily clamped. Usually several bone anchoring devices are necessary. The screw members are then screwed into the bone or a vertebra and then the receiving parts are pivoted by applying a force to overcome the clamping force until each receiving part has the correct orientation for the insertion of the rod. Due to the temporary clamping, the receiving part 5 is held in this angular position. The rod 20, which connects the bone anchoring devices, is inserted and the inner screw 7 is tightened to move the pressure element 6 downwards to lock the head 4 so that the angular position of the screw member 2 with respect to the receiving part 5 is fixed. The rod 20 is then fixed by the inner screw 7.

Modifications of the previously described embodiment are conceivable. In a first modification, the notches have a substantially constant depth over their length. In this case, the interference fit between the notch and the projection is achieved over the length of the notch. The assembly and disassembly of the receiving part and the pressure element needs then larger forces. In a further modification, only one projection and one recess or notch is present. In a still further modification more than two projections and corresponding recesses are provided. In another modification the recess is provided at the receiving part and the projection is provided at the pressure element. In this modification, the recess is open toward the top end 51 and closed toward the bottom end 52 of the receiving part.

For the anchoring element all kinds of anchoring elements can be used and combined with a receiving part. These anchoring elements are e.g. screws of different length, with different diameters, cannulated screws, screws with different thread forms, nails, etc.

Various kinds of receiving parts can be used in particular such with different locking devices. For example, instead of the one-part locking device such as the inner screw that locks the rod and the head simultaneously, a two-part locking devices with an outer screw and an inner screw can be used. In this case the pressure element has a U-shaped recess with legs extending above the rod. With the two-part locking device the head and the rod can be fixed independently. Further, outer nuts, outer caps, bayonet locking devices or others are also possible. The shape of the receiving part is not limited to the embodiment shown. For example, the receiving part can have an asymmetric end portion for allowing a greater pivot angle of the screw member to one side.

In a further modification, the receiving part is configured to allow the introduction of the screw element from the bottom end.

The invention claimed is:

1. A bone anchoring device comprising:
an anchoring element having a shaft for anchoring to a bone and a head,
a receiving part having a longitudinal axis from a top end to a bottom end, a rod recess for receiving a rod therein, a coaxial bore extending from the top end in the direction of the bottom end and a seat for receiving the head near the bottom end, and
a pressure element that is movable within the bore;
wherein the head is pivotable with respect to the receiving part and configured to be fixed at an angle by exerting pressure via the pressure element onto the head when the anchoring element and the pressure element are in the receiving part;
wherein the pressure element has an outer wall portion having a first feature, wherein the first feature is one of a recess or a projection and wherein the receiving part has an inner wall portion having a second feature, wherein the second feature is the other of a recess or a projection that cooperates with the first feature of the pressure element;
wherein the pressure element is configured to assume a first position within the bore of the receiving part wherein the recess and the projection are engaged to allow the pressure element to exert a preload onto the head and the head is prevented from freely pivoting but is not locked;
wherein the pressure element is movable along the longitudinal axis from an assembly position spaced from the bottom end of the receiving part wherein the recess and the projection are disengaged and the first feature is entirely above the second feature along the longitudinal axis to the first position closer to the bottom end of the receiving part wherein the recess and projection are engaged;
wherein, when the pressure element is in the assembly position, the projection and the recess are disengaged, a portion of the projection and an opening to the recess are aligned along an axis parallel to the longitudinal axis and the portion of the projection and the opening radially overlap, and the head is capable of freely pivoting; and
wherein the recess is inclined along the longitudinal axis such that when the pressure element is moved downward in the receiving part between the assembly position and the first position, a pressure force between the recess and the projection increases.

2. The bone anchoring device of claim 1, wherein the pressure element is configured to assume a second position wherein the pressure element exerts a locking pressure on the head such that the head is locked.

3. The bone anchoring device of claim 1, wherein the assembly position is one of several assembly positions wherein the head is capable of freely pivoting.

4. The bone anchoring device according to claim 3, wherein the pressure element is movable out of the first position into one of the assembly positions by pressing the head against the pressure element.

5. The bone anchoring device of claim 1, wherein the projection and the recess are sized to form an interference fit between the projection and the recess when the pressure element is in the first position.

6. The bone anchoring device of claim 1, wherein a radial dimension of the recess varies in a direction coaxial with a bore axis of the bore of the receiving part.

7. The bone anchoring device according to claim 1, wherein the radial dimension of the projection that engages the recess is substantially constant.

8. The bone anchoring device according to claim 1, wherein the inner wall portion of the receiving part has a projection and the outer wall portion of the pressure element has a recess.

9. The bone anchoring device according to claim 8, wherein the recess is a notch with a substantially V-shaped cross section that is open at an end of the pressure element facing the head of the anchoring element and that has a decreasing depth towards an end of the pressure element opposite to the head when the bone anchoring device is assembled.

10. The bone anchoring device of claim 1, wherein the recess is a notch that extends coaxially with a bore axis of the bore of the receiving part.

11. The bone anchoring device according to claim 1, wherein the projection is a tip obtained by crimping.

12. The bone anchoring device of claim 1, wherein the pressure element has a rod recess on its side facing away from the head for receiving the rod that is aligned to the rod recess of the receiving part when the bone anchoring device is assembled and wherein the projection and the recess are arranged at 90° with respect to the rod recesses.

13. The bone anchoring device according to claim 1, wherein at least two pairs of cooperating recesses and projections are provided.

14. The bone anchoring device of claim 1, wherein a fixation element is provided for fixing the rod.

15. The bone anchoring device of claim 1, wherein the pressure element is continuously movable from the assembly position in which the head is freely pivotable to the first position by exerting pressure onto an end of the pressure element facing away from the head of the anchoring element.

16. The bone anchoring device of claim 1, wherein the receiving part and the pressure element are each formed in one piece.

17. The bone anchoring device of claim 16, wherein the projection and the recess are configured to cooperate without spring portions provided at either the receiving part or the pressure element.

18. The bone anchoring device of claim 16, wherein the pressure element is formed integrally with the first feature, and wherein the receiving part is formed integrally with the second feature.

19. A bone anchoring device comprising:
an anchoring element having a shaft for anchoring to a bone and a head,
a receiving part having a longitudinal axis from a top end to a bottom end, a rod recess for receiving a rod therein, a coaxial bore extending from the top end in the direction of the bottom end and a seat for receiving the head near the bottom end, and
a pressure element that is movable within the bore, the pressure element having a U-shaped recess for receiving the rod;
wherein the head is pivotable with respect to the receiving part and configured to be fixed at an angle by exerting pressure via the pressure element onto the head when the anchoring element and the pressure element are in the receiving part;
wherein the pressure element has an outer wall portion having a first feature, wherein the first feature is one of a recess or a projection and wherein the receiving part has an inner wall portion having a second feature, wherein the second feature is the other of a recess or a projection that cooperates with the first feature of the pressure element;
wherein the pressure element is configured to assume a first position within the bore of the receiving part wherein the recess and the projection are engaged to allow the pressure element to exert a preload onto the head and the head is prevented from freely pivoting but is not locked;
wherein the pressure element is movable along the longitudinal axis from an assembly position spaced from the bottom end of the receiving part wherein the recess and the projection are disengaged to the first position closer to the bottom end of the receiving part wherein the recess and projection are engaged;
wherein, when the pressure element is in the assembly position, the projection and the recess are disengaged, the projection and an opening to the recess are aligned along an axis parallel to the longitudinal axis and the head is capable of freely pivoting; and
wherein the projection is located below a bottommost portion of the U-shaped recess of the pressure element when the anchoring element and the pressure element are in the receiving part; and
wherein the recess is inclined along the longitudinal axis such that when the pressure element is moved downward in the receiving part between the assembly position and the first position, a pressure force between the recess and the projection increases.

20. A bone anchoring device comprising:
an anchoring element having a shaft for anchoring to a bone and a head,
a receiving part having a longitudinal axis from a top end to a bottom end, a rod recess for receiving a rod therein, a coaxial bore extending from the top end in the direction of the bottom end and a seat for receiving the head near the bottom end, and
a pressure element that is movable within the bore;
wherein the head is pivotable with respect to the receiving part and configured to be fixed at an angle by exerting pressure via the pressure element onto the head when the anchoring element and the pressure element are in the receiving part;
wherein the pressure element has an outer wall portion having a first feature, wherein the first feature is one of a recess or a projection and wherein the receiving part has an inner wall portion having a second feature, wherein the second feature is the other of a recess or a projection that cooperates with the first feature of the pressure element;

wherein the pressure element is configured to assume a first position within the bore of the receiving part wherein the recess and the projection are engaged to allow the pressure element to exert a preload onto the head and the head is prevented from freely pivoting but is not locked;

wherein the pressure element is movable along the longitudinal axis from an assembly position spaced from the bottom end of the receiving part wherein the recess and the projection are disengaged to the first position closer to the bottom end of the receiving part wherein the recess and projection are engaged;

wherein, when the pressure element is in the assembly position, the projection and the recess are disengaged, the projection and an opening to the recess are aligned along an axis parallel to the longitudinal, and the head is capable of freely pivoting;

wherein the inner wall portion of the receiving part has a projection and the outer wall portion of the pressure element has a recess; and wherein the recess is a notch with a substantially V-shaped cross section that is open at an end of the pressure element facing the head of the anchoring element and that has a decreasing depth towards an end of the pressure element opposite to the head.

* * * * *